United States Patent [19]

Kahn

[11] 4,095,950
[45] Jun. 20, 1978

[54] METHOD FOR THE CHROMATOGRAPHIC ANALYSIS OF A TECHNETIUM-CONTAINING MIXTURE

[75] Inventor: Stephen Kahn, Walnut Creek, Calif.

[73] Assignee: Bio-Dynamics, Inc., Indianapolis, Ind.

[21] Appl. No.: 695,108

[22] Filed: Jun. 11, 1976

[51] Int. Cl.$^2$ ............................................. G01N 31/08
[52] U.S. Cl. ................................. 23/230.3; 23/230 B; 73/61.1 C; 210/31 C
[58] Field of Search .............. 23/230.3, 230 R, 230 B; 250/303; 73/61.1 C; 210/31 C, 24 C; 424/1.5

[56] References Cited

U.S. PATENT DOCUMENTS

| | | | |
|---|---|---|---|
| 3,046,779 | 7/1962 | Coleman | 73/61.1 C |
| 3,725,295 | 4/1973 | Eckelman et al. | 23/230.3 X |
| 3,873,680 | 3/1975 | Jackson et al. | 250/303 X |
| 3,914,174 | 10/1975 | Fuchs | 210/31 C |

OTHER PUBLICATIONS

Eckelman et al., "Analytical Pitfalls with Techetium-99m-labeled Compounds", Chemical Abstracts, vol. 77, 1972, No. 2428J.

*Primary Examiner*—Morris O. Wolk
*Assistant Examiner*—Arnold Turk
*Attorney, Agent, or Firm*—Woodard, Weikart, Emhardt & Naughton

[57] ABSTRACT

Method for the chromatographic analysis of a technetium-containing mixture of bound, reduced technetium; unbound, reduced technetium; and, free pertechnetate. A portion of the mixture is spotted on a chromatographic adsorbent, preferably cellulose-fiber paper, and is developed with an aqueous salt solution, preferably comprising sodium chloride and/or sodium pyrophosphate. The developed chromatogram has an isolated zone in which the unbound, reduced technetium is located. Simultaneously therewith, a second chromatogram is developed utilizing a suitable liquid organic solvent, preferably comprising a mixture of acetone and acetic acid. The developed chromatogram has an isolated zone in which the free pertechnetate is located. Radioactive measurements are made and the amounts of unbound, reduced technetium and of free pertechnetate are determined as proportions of total technetium. The amount of bound, reduced technetium may then be readily calculated. An elutable or chromatographic dye is preferably located on the adsorbent prior to development. The dye separates into colored regions which serve to indicate the completion of development, the approximate area of separation between the regions of the technetium states and the propriety of the technique used in performing the analysis.

20 Claims, No Drawings

METHOD FOR THE CHROMATOGRAPHIC ANALYSIS OF A TECHNETIUM-CONTAINING MIXTURE

BACKGROUND OF THE INVENTION

1. Field of the Invention

This invention relates to a method for the analysis of technetium present in a mixture as free pertechnetate and bound and unbound, reduced technetium, and more particularly to such a method involving chromatographic techniques.

2. Description of the Prior Art

Radioisotopes have many diagnostic and therapeutic applications in the field of medicine. The various isotopes display differing types and energy levels of radiation, minimum retention times in the body and affinities for body organs and tissue. The selection of an isotope for a particular therapeutic or diagnostic application is dependent upon these varying characteristics.

Technetium, having an atomic number of 43 and an atomic weight of 99, has been used in medical procedures such as for scanning the liver. In preparing the technetium for this type of procedure, it is bound to a carrier such as diphosphonate, polyphosphate, pyrophosphate; iron-ascorbate-DTPA or human serum albumin. In preparing the test solution, however, not all of the technetium will become bound to the carrier. Technetium will primarily assume either a hydrolyzed or reduced state in which the technetium has a charge of +4, or it may assume an oxidized state with a charge of +7. A portion of the reduced technetium will become bound to the carrier, and the remaining reduced technetium will generally be unbound. The oxidized technetium generally is present as free pertechnetate ions having a chemical formula of $TcO_4^{31}$. The various chemical states define where the radioactivity will locate in a patient, and it is therefore extremely important to determine the amounts of the various states in the test solution before administering it to a patient.

A method which has been used in the quantitative analysis of a technetium-containing mixture is chromatography. One test involving this technique is the Qualitrol-S system which is marketed by New England Nuclear of North Billerica, Massachusetts. The Qualitrol procedure is designed for use with technetium which is bound to a sulfur colloid carrier. The Qualitrol procedure utilizes the known technique of ascending, thin layer chromatography using silica gel as the support phase or adsorbent, and physiological saline as the developing solvent. A sample of the technetium-containing mixture is spotted on the strip impregnated with silica gel and is air dried. The strip is then placed with one end in contact with the saline solvent and the solvent migrates upwardly. The technetium present as free pertechnetate is transported upwardly with the solvent. The strip is then cut into two pieces and the percentage of free pertechnetate is measured as a ratio of the radioactivity of the top section of the strip to the radioactivity of the entire strip. An estimate of the amount of technetium present as bound technetium is obtained by assuming that all of the technetium is present as either bound technetium or free pertechnetate.

The Qualitrol system does provide a ready means for estimating the amount of bound technetium in a sulfur colloid system. The Qualitrol technique does, however, entail certain drawbacks. The Qualitrol technique is not well suited, for example, for use with a technetium-containing mixture in which there is a possibility of having hydrolyzed reduced technetium. The technetium mixture is dried and developed in air and the presence of reduced technetium will tend to give false positive results for free pertechnetate due to air oxidation. In addition, the accuracy of the estimate as to the amount of bound, reduced technetium becomes correspondingly less accurate as the amount of unbound, reduced technetium present increases. It is also disadvantageous to use the thin layer chromatography support paper which is generally more fragile and therefore more difficult to use than some other support media.

The Seprachrom procedure of the Gelman Instrument Company of Ann Arbor, Michigan, discloses several related chromatography procedures for the analysis of technetium-containing mixtures. The Seprachrom procedures utilize ascending chromatography in conjunction with an instant thin layer chromatography sheet of glass microfiber impregnated with silica gel or polysilicic acid. The technetium-containing mixture is spotted on the support medium and is developed with 85% methanol in most instances, although the same chromatogram is redeveloped with normal saline solution when the carrier is sulfur colloid and with a solvent comprising N-butanol, ethanol and water when the carrier is iron-ascorbate-DTPA. The developing results in the free pertechnetate ions migrating with the solvent to the top of the support medium. The paper is divided and the proportion of the free pertechnetate present is determined by the radioactivity measurements. As in the Qualitrol system, the amount of bound technetium in the technetium-containing mixture is estimated to be the difference between the percentage of free pertechnetate and 100%. The Seprachrom procedure therefore has the disadvantage of failing to provide a fully accurate measurement of the amount of bound, reduced technetium. The Seprachrom procedure also requires a substantial amount of time which may range from between 25 to 60 minutes, and the use of the relatively fragile, instant thin layer chromatography media may also present difficulties.

A third chromatography procedure for the analysis of technetium-containing mixtures has been disclosed by Cooper and Zimmer of the Medical College of Wisconsin, Milwaukee, Wisconsin, in a paper entitled "Radiochemical Purity and Stability of Commercial TC-99m-Stannous DTPA Kits Using a New Chromatography Technique," appearing in the Journal of Nuclear Medicine Technology, Vol. 3, p. 208 (1975). The Zimmer procedure utilizes ascending chromatography on Gelman instant thin layer chromatography strips impregnated with silica gel. A sample of the technetium-containing mixture is spotted on the supporting strip and is fully developed with acetone. The strip is then air dried and redeveloped with normal saline solution. The progress of the migrating saline solution is watched carefully and the development is stopped when the saline solution has reached approximately the center of the developed strip. The strip is then cut into three pieces and the proportionate amount of bound, reduced technetium is determined as the ratio of the radioactivity of the center section to the radioactivity of the entire strip.

The Zimmer procedure therefore provides a direct and accurate measurement of the bound, reduced technetium present in the sample, and may be advantageously used in certain circumstances. The Zimmer procedure does, however, have certain disadvantages when used in other instances. Primarily, the second, partial development with normal saline must be monitored closely to prevent distortion of the test results. If the normal saline is not permitted to migrate the proper extent along the supporting strip, then the radioactivity of the center section will not accurately represent the amount of bound, reduced technetium present in the technetium-containing mixture. The support medium being the instant thin layer chromatography type also presents the handling problems inherent in dealing with a relatively fragile material. Finally, the fact that the same supporting strip must be developed, dried and redeveloped extends the length of time required to complete the analysis. This latter problem is complicated by the fact that the need to divide the paper into three sections generally means that the paper must be longer than for those procedures in which the paper is only cut into two pieces, since the potential for error would otherwise be increased. As a result, the Zimmer procedure is not well suited to such uses as hospital quality control, although it is appropriate for laboratory work.

The development of simultaneous chromatograms is known in the art in the sense that doing more than one thing at a time saves time. Examples of patents disclosing devices designed to facilitate simultaneous performance of two or more chromatographic separations are U.S. Pat. Nos. 3,686,118, issued to Benson on Aug. 22, 1972; U.S. Pat. No. 3,513,092, issued to Matherne on May 19, 1970; U.S. Pat. No. 3,458,437, issued to Ouano on July 29, 1969; an U.S. Pat. No. 3,194,400 issued to Herndon on July 13, 1965. The analysis techniques described above and relating to technetium mixtures have been unable to use the time saving aspect of simultaneous development to any significant advantage.

With the increasing use of radioisotopes, such as technetium, in medicinal applications, and the concomitant need for quality control of such materials, there has arisen a need for a simple and accurate procedure for qualitative analysis of technetium-containing mixtures. The existing techniques have been successfully used for their intended purposes. There remains, however, the desire for an analysis technique which is easy for all persons to perform, and which provides the accuracies required by modern medical applications.

In efficiently and accurately performing chromatographic analyses of this type, it is necessary to permit development of the chromatograms to be complete, while not waiting unnecessarily long after full development to finish the analysis. It is also highly advantageous to know the precise demarcation between the separate zones of the chromatograms for accurate analysis of them. In U.S. Pat. No. 3,046,779, issued to Coleman on July 31, 1962, there is disclosed the use of a ball point pen to draw a line on a paper adsorbent perpendicular to the start line of the solvent. As the solvent migrates longitudinally of the pen line, the ink distorts to indicate the progress of the solvent front. The ink line thereby indicates completion of development, although it does not assist in determining the location of the separated zones of the test sample. An identification system using chromatographic dyes is disclosed in U.S. Pat. No. 3,914,174, issued to Fuchs on Oct. 21, 1975. The adsorbent is coated, preferably by spraying, with two or more different dyestuffs. When an unknown solvent is spotted on the prepared adsorbent, a ring chromatogram characteristic of the particular solvent is formed and the solvent may thereby be identified. The dye does not serve to indicate the completion of the developing or the location of particular zones of the test sample.

SUMMARY OF THE INVENTION

Disclosed herein is a method for the chromatographic analysis of a technetium-containing mixture of bound, reduced technetium; unbound, reduced technetium, and, free pertechnetate. A first sample of the technetium-containing mixture is spotted on a first chromatographic adsorbent, and is developed with an aqueous salt solution. The salt solution migrates along the first adsorbent and through the first sample, ultimately transporting the bound, reduced technetium and the free pertechnetate to a second zone, away from the unbound, reduced technetium which remains in a first zone. A second sample of the technetium-containing mixture is spotted on a second adsorbent and is developed with a suitable liquid organic solvent. The developing results in the free pertechnetate being transported to a fourth zone, away from the bound and unbound reduced technetium, which remains in a third zone. The technetium present in one zone in each of the first and second adsorbents is measured and the amount of bound, reduced technetium present in the technetium-containing mixture may then be calculated by mathematical analysis.

To facilitate the determination of the amount of the separated components, a chromatographic dye is located on each of the adsorbents near the location of the first and second samples. As the chromatograms are developed, a portion of the dye is transported by the respective developing solution. The chromatographic separation of the components of the dye results in a visible indicator of the approximate demarcation of the separated technetium states. In certain applications, the adsorbent may be divided physically along this demarcation and the radioactivity of the separate portions may be easily measured.

It is an object of the present invention to provide a method of chromatographic analysis for determining the amount of technetium present in each of the states of free pertechnetate and of bound and unbound, reduced technetium.

A further object of the present invention is to provide a method of analysis of the type described which yields accurate results, and which may be easily performed.

Another object of the present invention is to provide a method of chromatographic analysis for a technetium-containing mixture for which the amounts of each of the technetium states may be determined, and for which the time required to complete the analysis is less than about 10 minutes.

It is a further object of the present invention to provide a method of chromatographic analysis which meets the above requirements and which utilizes the relatively strong, cellulose-fiber chromatography paper.

It is yet another object of the present invention to provide a method of chromatographic analysis of a technetium-containing mixture which is suitable as a quality control technique in nuclear medicine facilities.

A further object of the present invention is to provide a method of chromatographic analysis of the above type which may be easily and practically performed by a hospital technician or the like a very short time prior to administration of the technetium-containing mixture to a patient.

Another object of the present invention is to provide a method of analysis meeting the above-described requirements, and which may be performed with a minimum of supervision and expenditure of time.

Further objects and advantages of the present invention will become apparent from the description which follows.

DESCRIPTION OF THE PREFERRED EMBODIMENTS

The chromatographic procedure of the present invention provides a simple and accurate method for determining the amount of technetium present in each of three chemical states within a given mixture. Technetium having an atomic weight of 99 is one of the most common species for use in nuclear medicine and is employed, for example, to obtain diagnostic scans of the kidney. The technetium dose is typically prepared a short time prior to administration to a patient. The technetium may be added, for example, to a stannous-containing radiopharmaceutical kit which ideally reduces the technetium from the $+7$ state to the $+4$ state and results in the technetium becoming chemically bound to a carrier matrix. In practice, however, it has been found that unbound, reduced technetium and/or oxidized technetium generally in the form of free pertechnetate may exist along with the bound, reduced technetium. The presence of either the unbound, reduced technetium or the free pertechnetate in amounts larger than a few percent in the administered dose, will result in interference with the diagnostic scan or picture. It is therefore highly desirable to have a method of quality control for analyzing the technetium-containing mixture prior to administration.

In accordance with the present invention, separate and preferably simultaneous chromatograms for two samples of the technetium-containing mixture are obtained. The chromatographic analyses generally involve the placement of a sample of the technetium-containing mixture on a support medium or adsorbent. The chromatogram is developed without drying by contacting the adsorbent with a developing liquid. The development occurs as the developing liquid migrates across the adsorbent and through the sample of the technetium-containing mixture. Due to the different affinities of the various chemical states of the technetium between the mobile phase or developing solution and the stationary phase or adsorbent, certain of the states of the technetium will be transported by the developing solution away from the remaining technetium states. Analysis of the developed chromatogram permits the values of the various technetium states to be calculated.

The principles of the present invention may be utilized in conjunction with any chromatographic adsorbent. Thin layer chromatography media typically include a thin layer of an adsorbent coating, such as silica gel, supported on a glass, plastic or metal sheet. Instant thin layer chromatography media generally comprise a glass mylar or glass microfiber support impregnated with an adsorbent such as silica gel, silicic acid or cellulose. The disclosure in U.S. Pat. No. 3,914,174, issued to Fuchs on Oct. 21, 1975, is hereby incorporated by reference as listing a number of the alternative adsorbent media with which the method of this invention may be performed. It is preferred, however, to perform the method of the present invention with standard chromatography paper, which generally comprises cellulose-fiber paper such as Whatman chromatography paper. The standard paper is preferred since the thin and instant thin layer chromatography media are considerably more fragile and therefore more difficult to handle successfully. Due to the shorter length of development time for the present analysis, the standard paper may be practically used. The use of standard paper in conjunction with certain of the prior art techniques would be impractical due to the analysis technique requiring a substantial amount of time.

The present invention may be performed with a technetium carrier which is elutable, and these include but are not limited to pyrophosphate, polyphosphate, diphosphonate and DTPA.

Development in accordance with standard ascending chromatographic techniques is preferred since that technique is easy to perform and does not involve unduly long development time, although other known techniques may be employed. The short length of time required to complete the analysis according to the present invention makes it particularly simple to utilize the ascending chromatography technique. The relatively strong and self-supporting standard chromatography paper may be successfully used, minimizing the problems of properly supporting the adsorbent during development.

A first chromatogram is developed in which the bound, reduced technetium and the free pertechnetate are separated from the unbound, reduced technetium. A sample of the technetium-containing mixture is spotted on a chromatographic adsorbent. The adsorbent is then developed by contacting it with a reservoir of an aqueous salt solution which may comprise, for example, sodium chloride, magnesium sulfate, sodium pyrophosphate, potassium bromide, sodium iodide or potassium chloride. Development with an aqueous solution of sodium chloride is preferred.

As a result of the development, two distinct zones are present on the adsorbent. One zone contains the unbound, reduced technetium generally at the location where the sample of the technetium-containing mixture was originally placed. The other zone contains the bound, reduced technetium and the free pertechnetate, both of which have migrated away from the unbound, reduced technetium.

A second chromatogram is developed in which the free pertechnetate is separated from the bound and unbound, reduced technetium. In this second procedure, ascending chromatography in conjunction with standard, cellulose-fiber chromatography paper is the preferred procedure, although again the other chromatographic media and techniques could also be utilized. The adsorbent for the second chromatogram is developed with a suitable liquid organic solvent which may include, for example, acetone, an acetone-acetic acid mixture, ethanol, propanol, methanol, methyl ethyl ketone or n-butanol. A mixture of acetone and acetic acid is preferred, however, due to the generally lower cost and greater availability of these organic solvents. As a result of the development of the second chromatogram, the free pertechnetate is transported to a zone away from the bound and unbound, reduced technetium, which remains in a separate zone.

Upon completion of the two chromatograms, the three technetium states have been divided into four distinct zones which contain: first zone, unbound, reduced technetium; second zone, free pertechnetate and bound, reduced technetium; third zone, bound and unbound, reduced technetium; fourth zone, free pertechnetate. By measuring the technetium present in at least one of the zones on each chromatogram, and with other information, the amount of bound, reduced technetium may be calculated. The first and fourth zones may be measured, for example, if the total amount of technetium in each sample is known. The amounts of unbound, reduced technetium and free pertechnetate could then be determined and the amount of bound, reduced technetium could be readily ascertained. Mathematical analyses of other variations of known and measured information would similarly permit values for each of the technetium states to be calculated. One method for calculating the percentage of bound, reduced technetium in a sample is described in detail in Example I. The percentage of unbound, reduced technetium is determined by the proportional radioactivity of the first zone to the radioactivity of the first and second zones combined. The percentage of free pertechnetate was determined as the proportion of the radioactivity of the fourth zone to the combined radioactivity of the third and fourth zones. The percentage of bound, reduced technetium is then determinable as the percentage of radioactivity not attributable to the unbound, reduced technetium and the free pertechnetate, the latter percentages having been calculated as described. This method of analysis encompasses the determination of the percentage of technetium found in one of the zones of the first chromatogram, and in one of the zones of the second chromatogram. As exemplified in Example I, the percentages of technetium in the respective zones is determined by measuring the radioactivity of the technetium found in each of the four zones and deriving appropriate fractions to arrive at a percentage value for the respective zones.

Another consideration which arises in connection with the development of the two chromatograms is the pH of the developing solution. In preparing the salt solution, for example, an aqueous solution of a particular salt at a given molarity or dilution will have a certain pH. The pH of the various salt solutions will vary for a particular molarity. It may therefore be desirable to adjust the pH with the addition of a suitable acid or base to obtain optimum conditions for development. This may be readily determined by preliminary tests. The same is true with respect to the organic solvent developing solution.

To assist in the performance of the analysis, a chromatographic dye is placed on the adsorbent near the location where the sample of the technetium containing mixture will be spotted. The dye is preferably placed on the adsorbent as a line extending transverse of the path along which the developing liquid is to migrate. In the preferred procedure utilizing ascending chromatography, the dye forms a line which extends horizontally when the adsorbent is positioned for development. If the adsorbent is standard chromatography paper, as is preferred, then the line would extend widthwise across the paper surface and would be oriented horizontally when the paper is supported vertically during development. For the purposes herein, the term vertically in reference to the orientation of the chromatography paper is defined as referring to the usual orientation of such paper when performing ascending chromatography as is well known in the art.

In addition to being located near the spotted sample of the technetium-containing mixture, the dye may serve as an indicator of the location at which the sample is to be spotted. This load line should then be properly positioned along the adsorbent in accordance with the chromatography technique being employed. In this respect, the dye serves also to indicate if the developing liquid has improperly contacted the sample directly, since the developing liquid would then be colored by the dye.

As the development of the chromatogram progresses, a portion of the dye will migrate with the developing liquid. The dye is thereby separated into distinct regions of different colors, depending upon the affinities of the dye components to the developing liquid. The migration of the color with the developing liquid serves to indicate the progress of the development, and will signal completion of the chromatogram when the migrating color reaches the desired point. The demarcation between the colors into which the dye has separated serves also as an approximate indicator of the separation point between the zones of the technetium states as previously described. In using an adsorbent which may be physically divided, the division may be made generally at the demarcation between the two colors, and the technetium zones will be appropriately separated also. Subsequent to this division, the different colors of the dye also serve as an indicator of the contents of the two pieces to ensure that proper analysis of the chromatogram is made. U.S. Pat. No. 3,914,174, issued to Fuchs on Oct. 21, 1975 is again hereby incorporated by reference as listing a number of dyestuffs which are suitable for use in the present technique. The appropriate selection and concentration of the dyestuffs for use with a particular developing solvent can be readily ascertained by means of preliminary tests.

EXAMPLE I

A technetium-containing mixture was obtained by adding technetium to a stannous-containing radiopharmaceutical kit in accordance with the instructions for preparing the technetium for administering to a patient.

Two chromatography chambers were labeled for a normal saline solution and an acetone-acetic acid mixture, respectively. Enough of each of the two solvents was added to the appriate chamber to have 1-2 mm of liquid between the center of the chamber bottom and the center of the meniscus. The chambers were kept closed except when adding the solvent and when inserting or removing the chromatogram.

A 5-10 ul drop of the technetium-containing mixture was placed on a precolored load line on each of two pieces of standard, cellulose-fiber chromatography paper. The load lines were made by marking the papers with commercial, felt tip pens, each commercially available as a "Bic Banana" pen, manufacturer's number IC-20, sold by Bic Pen Corp., Milford, Connecticut 06460.

The load lines were green and black and were widthwise lines located about one-half inch from one end of the papers. The first paper with the green load line was placed immediately in the chamber containing the normal saline solution. The second paper was similarly inserted into the chamber containing the acetone-acetic acid mixture. Care was taken to prevent the colored load lines from being immersed in the solvent and to prevent the papers from adhering to the sides of the chambers.

Color from the green and black load lines reached the top of each paper in 2-3 minutes and the papers were removed and dried. The top two-thirds or 1¼ inches of the paper developed in normal saline were green in color; the bottom one-third or three-fourth inch was white. The paper was divided at the border of the colors and a sodium iodide detector was used to count the radioactivity of each of the two pieces. The paper developed in the acetone-acetic acid mixture had a top one-third or ¾ inch which was purple; the bottom two-thirds or 1½ inches were brown. This paper was also divided at the demarcation between the two colors and the radioactivity of each piece was counted. In accordance with good chromatography technique, each count must be corrected for counting geometry, counting time, coincidence loss and background, as required.

The corrected counts for the strips were: white strip 5,355; green strip 233,500; purple strip 1,317; and, brown strip 176,800. The percentage of the unbound, reduced technetium was calculated to be 2.24% according to the formula:

$$\% \text{ unbound, reduced} = \frac{100 \text{ (white count)}}{\text{(white count)} + \text{(green count)}}$$

The percentage of the technetium present as free pertechnetate was calculated to be .74% according to the formula:

$$\% \text{ free pertechnetate} = \frac{100 \text{ (purple count)}}{\text{(purple count)} + \text{(brown count)}}$$

The percentage of bound, reduced technetium therefore was 97.02%. The total analysis procedure required less than 10 minutes to perform.

EXAMPLES II–VI

The procedure of Example I was followed fully except that, instead of using a normal saline solution, aqueous solutions of magnesium sulfate, sodium chloride and sodium pyrophosphate, potassium bromide, potassium chloride and sodium iodide were used to develop the first paper. The development times and test results were substantially the same as those of Example I.

EXAMPLES VII–XI

The procedure of Example I was followed fully except that the second paper was developed with ethanol, propanol, methanol, methyl ethyl ketone and n-butanol. The development times and test results were similar to those of Example I.

EXAMPLE XII–XIV

The procedure of Example I was followed fully except that in place of the standard chromatography paper, the adsorbent for each of the chromatograms was glass mylar impregnated with silica gel, glass microfiber impregnated with silicic acid, and a thin layer chromatography adsorbent of silica gel coated on an aluminum backing. The test results obtained were substantially the same as those of Example I. The development times were slightly longer for the thin layer chromatography adsorbent, however. In addition, the thin and instant thin layer chromatography media were more difficult to handle than the standard chromatography paper.

EXAMPLE XV

The procedure of Example I was followed fully except that the chromatograms were developed with the chambers open to the air. Acceptable results were obtained, although the value calculated for the bound, reduced technetium was slightly less than determined in Example I. This is believed to be the result of air oxidation of the tin from stannous to stannic, followed by the oxidation of some of the bound, reduced technetium in the test sample.

EXAMPLE XVI

The procedure of Example I was followed fully except that the chromatograms, subsequent to development, were wet-wrapped in cellophane tape rather than being air dried. Identical results to those in Example I were obtained.

EXAMPLES XVII–XX

The procedure of Example I was followed fully except that the load lines on the first and second papers, respectively, were marked with dyestuffs corresponding to the Color Index for Acid Orange and Solvent Red; Acid Blue and Solvent Blue; Acid Blue and Solvent Yellow; Solvent Blue with Solvent Yellow and Solvent Red. Suitable results were obtained.

The invention claimed is:

1. A method for the chromatographic analysis of a technetium-containing mixture of unbound, reduced technetium, free pertechnetate, and reduced technetium bound to an elutable carrier, the method being for determining the percentage of the bound, reduced technetium present in the mixture without requiring isolation of the bound, reduced technetium from the other technetium components, comprising the steps of:
   a. placing a first sample of the technetium-containing mixture on a first chromatographic adsorbent;
   b. developing the first adsorbent with an aqueous salt solution to transport the free pertechnetate and the bound, reduced technetium to a second zone away from the unbound, reduced technetium remaining in a first zone;
   c. placing a second sample of the technetium-containing mixture on a second chromatographic adsorbent;
   d. developing the second solvent adsorbent with a suitable liquid organic solvent to transport the free pertechnetate to a fourth zone away from the bound, reduced technetium and the unbound, reduced technetium remaining in a third zone;
   e. determining the radioactivity of the technetium present in at least zones one and four of said first and second adsorbents and
   f. calculating the percentage amount of bound, reduced technetium present in the mixture.

2. The method of claim 1 in which said developing of steps b. and d. are performed essentially simultaneously.

3. The method of claim 1 in which in the determining of step e. includes determining the radioactivity in each of the four zones and in which the calculating of step f. includes calculating the percentage of the radioactivity of the unbound, reduced technetium in the first zone with respect to the combined radioactivity of the first and second zones and calculating the percentage of the radioactivity of the free pertechnetate in the fourth zone with respect to the combined radioactivity of the third and fourth zones.

4. The method of claim 1 in which said developing of steps b. and d. is performed by orienting the adsorbents vertically and by contacting the bottom portion of the adsorbents with the aqueous salt solution and the organic solvent, the salt solution and organic solvent migrating upwardly along the first and second adsorbents, respectively.

5. The method of claim 4 in which an elutable dyestuff is located on one of the adsorbents, near the location of said placing of the sample of the technetium-containing mixture on the adsorbent, and prior to said developing of the adsorbent, the dyestuff extending horizontally along the adsorbent when the adsorbent is positioned for said developing.

6. The method of claim 1 in which an elutable dyestuff is located on one of the adsorbents, near the location of said placing of the sample of the technetium-containing mixture on the adsorbent, and prior to said developing of the adsorbent.

7. The method of claim 6 in which the first adsorbent comprises a cellulose fiber strip, the elutable dyestuff being located on the first adsorbent, the first adsorbent being about 2 and ¼ inches long and the elutable dyestuff being located about one-half inch from one end of the first adsorbent.

8. The method of claim 6 in which the sample of the technetium-containing mixture is placed directly upon the elutable dyestuff on the adsorbent.

9. The method of claim 1 in which the first adsorbent comprises a cellulose fiber strip.

10. The method of claim 9 in which the first adsorbent is about 2 and ¼ inches long.

11. The method of claim 9 in which the developing of the first adsorbent is conducted for less than about 10 minutes.

12. The method of claim 1 in which a portion of said developing of step b. is performed simultaneously with a portion of said developing of step d.

13. The method of claim 12 in which said developing of step b. is performed with an aqueous solution of sodium chloride and sodium pyrophosphate.

14. The method of claim 12 in which said developing of step d. is performed with a mixture of acetone and acetic acid.

15. The method of claim 12 in which said developing of step b. is performed with an aqueous solution of sodium chloride.

16. The method of claim 15 in which said developing of step d. is performed with a mixture of acetone and acetic acid.

17. The method of claim 16 in which the first and second adsorbents comprise cellulose fiber strips.

18. The method of claim 12 in which the first and second adsorbents comprise cellulose fiber strips.

19. The method of claim 18 in which said developing of steps b. and d. is performed by orienting the adsorbents vertically and by contacting the bottom portion of the adsorbents with the aqueous salt solution and the organic solvent, the salt solution and organic solvent migrating upwardly along the first and second adsorbents, respectively.

20. The method of claim 19 in which an elutable dyestuff is located on one of the adsorbents, near the location of said placing of the sample of the technetium-containing mixture on the adsorbent, and prior to said developing of the adsorbent, the dyestuff extending horizontally along the adsorbent when the adsorbent is positioned for said developing.

* * * * *